US009339427B2

(12) United States Patent
Martin et al.

(10) Patent No.: US 9,339,427 B2
(45) Date of Patent: May 17, 2016

(54) FIRST AID KIT WITH SPEECH, MUSIC, OR INSTRUCTIONAL SOUND EMISSION

(71) Applicant: Medline Industries, Inc., Mundelein, IL (US)

(72) Inventors: Tambra Martin, Trevor, WI (US); Brittany Johnson, Bristol, WI (US)

(73) Assignee: Medline Industries, Inc, Mundelein, IL (US)

( * ) Notice: Subject to any disclaimer, the term of this patent is extended or adjusted under 35 U.S.C. 154(b) by 0 days.

(21) Appl. No.: 14/445,768

(22) Filed: Jul. 29, 2014

(65) Prior Publication Data

US 2016/0030261 A1    Feb. 4, 2016

(51) Int. Cl.
| | |
|---|---|
| G08B 21/00 | (2006.01) |
| A61F 17/00 | (2006.01) |
| B65D 43/14 | (2006.01) |
| B65D 81/38 | (2006.01) |
| B65D 25/04 | (2006.01) |

(52) U.S. Cl.
CPC ............... *A61F 17/00* (2013.01); *B65D 25/04* (2013.01); *B65D 43/14* (2013.01); *B65D 81/3813* (2013.01); *B65D 2555/00* (2013.01)

(58) Field of Classification Search
CPC ........................................................ G08B 21/18
USPC .............. 340/691.1–692, 384.1, 384.6, 384.7
See application file for complete search history.

(56) References Cited

U.S. PATENT DOCUMENTS

| | | | |
|---|---|---|---|
| 3,798,806 A | 3/1974 | Sanford | |
| 4,102,067 A | 7/1978 | Tarrant | |
| 4,193,648 A * | 3/1980 | Gargiulo | G10F 1/06 108/152 |
| 4,525,393 A | 6/1985 | DiCostanzo | |
| 4,702,378 A * | 10/1987 | Finkel | A45C 11/00 206/581 |
| 4,704,934 A | 11/1987 | Nosrati et al. | |
| 4,791,741 A | 12/1988 | Kondo | |
| 4,882,966 A | 11/1989 | Silverman | |
| 4,973,087 A | 11/1990 | Balogh | |
| 5,108,338 A | 4/1992 | Margolis | |
| 5,115,472 A | 5/1992 | Park et al. | |
| 5,461,187 A | 10/1995 | Dudley | |
| 5,850,630 A * | 12/1998 | Wilson | G06F 19/3481 700/90 |

(Continued)

FOREIGN PATENT DOCUMENTS

| | | |
|---|---|---|
| EP | 277276 | 8/1988 |
| EP | 394573 | 10/1990 |
| WO | WO-2011139793 | 11/2011 |

OTHER PUBLICATIONS

"Notice of Allowance", U.S. Appl. No. 29/497,852, filed Jul. 29, 2014; Mailed May 29, 2015.

(Continued)

*Primary Examiner* — Jeffery Hofsass
(74) *Attorney, Agent, or Firm* — Philip H. Burns, IV

(57) ABSTRACT

A container (100) is provided with a container body (101) having a base (103) and a plurality of sidewalls (104,105) extending from the base to define a receiving cavity (200). A first container body part (201) is coupled to the container body to pivot between a closed position and an open position. One or more first aid items (203) are disposed within the receiving cavity. A sensor (207) detects the first container body part in or transitioning to open position. A sounder (208), operable with the sensor, emits one or more audible sounds (209) when the sensor detects the first container body part in or transitioning to the radially displaced open position.

19 Claims, 8 Drawing Sheets

(56) References Cited

U.S. PATENT DOCUMENTS

| | | | |
|---|---|---|---|
| 6,737,959 B2 | 5/2004 | Ho | |
| 7,203,726 B2 | 4/2007 | Hasegawa | |
| 7,658,280 B2 | 2/2010 | Bardet et al. | |
| 8,159,345 B2 * | 4/2012 | Stevens | G06Q 10/087 206/373 |
| 2008/0116088 A1 | 5/2008 | Roberts | |
| 2008/0116089 A1 | 5/2008 | Roberts | |
| 2008/0289230 A1 | 11/2008 | Mandelbaum et al. | |
| 2009/0070213 A1 | 3/2009 | Miller et al. | |
| 2009/0165343 A1 | 7/2009 | Miller et al. | |
| 2013/0159445 A1 | 6/2013 | Zonka et al. | |
| 2013/0305574 A1 | 11/2013 | Nelson et al. | |
| 2014/0311936 A1 * | 10/2014 | Marks | B65D 25/34 206/457 |

OTHER PUBLICATIONS

"Medline Catalog", ACE Elastic Bandage w/ Hook Closure by 3MHealthcare; *Medline Catalog*; http://www.medline.com/catalog/catalog.jsp; Unknown Publication date but believed to be prior to present application filing date.
"Medline Product Catalog", Adult Eye Patch by Flents; *Medline Catalog*; http://www.medline.com/catalog/catalog.jsp; Unknown Publication date but believed to be prior to present application filing date.
"Medline Catalog", Amerigel Hydrogel Gauze Dressing Packets by Amerx; *Medline Catalog*; http://www.medline.com/catalog/catalog.jsp; Unknown Publication date but believed to be prior to present application filing date.
"Medline Catalog", AmeriGel Hydrogel Gauze Dressings by Amerx; *Medline Catalog*; http://www.medline.com/catalog/catalog.jsp; Unknown Publication date but believed to be prior to present application filing date.
"Medline Catalog", Band-Aid (Multiple Prints) by Johnson & Johnson; *Medline Catalog*; http://www.medline.com/catalog/catalog.jsp; Unknown Publication date but believed to be prior to present application filing date.
"Medline Catalog", Band-Aid by Johnson & Johnson; *Medline Catalog*; http://www.medline.com/catalog/catalog.jsp; Unknown Publication date but believed to be prior to present application filing date.
"Medline Catalog", Band-Aid w/ Advanced Healing Blister Cushion by Johnson & Johnson; *Medline Catalog*; http://www.medline.com/catalog/catalog.jsp; Unknown Publication date but believed to be prior to present application filing date.
"Medline Catalog", Bioguard Large Gauze Roll by Derma Science; *Medline Catalog*; http://www.medline.com/catalog/catalog.jsp; Unknown Publication date but believed to be prior to present application filing date.
"Medline Catalog", Circus Stat Strip Bandages by Derma Sciences; *Medline Catalog*; http://www.medline.com/catalog/catalog.jsp; Unknown Publication date but believed to be prior to present application filing date.
"Medline Catalog", Clear Spot Bandages by Johnson & Johnson; *Medline Catalog*; http://www.medline.com/catalog/catalog.jsp; Unknown Publication date but believed to be prior to present application filing date.
"Medline Catalog", Coverlet Eye Occluders by Wilson Ophthalmic Corp; *Medline Catalog*; http://www.medline.com/catalog/catalog.jsp; Unknown Publication date but believed to be prior to present application filing date.
"Medline Catalog", Cuirty O-B Sponges by Covidien; *Medline Catalog*; http://www.medline.com/catalog/catalog.jsp; Unknown Publication date but believed to be prior to present application filing date.
"Medline Catalog", CURAD Antibacterial Adhesive Bandages; *Medline Catalog*; http://www.medline.com/catalog/catalog.jsp; Unknown Publication date but believed to be prior to present application filing date.
"Medline Catalog", CURAD Athletic Foam Bandages; *Medline Catalog*; http://www.medline.com/catalog/catalog.jsp; Unknown Publication date but believed to be prior to present application filing date.
"Medline Catalog", CURAD Butterfly Closure Adhesive Bandages; *Medline Catalog*; http://www.medline.com/catalog/catalog.jsp; Unknown Publication date but believed to be prior to present application filing date.
"Medline Catalog", CURAD Clear Adhesive Bandages; *Medline Catalog*; http://www.medline.com/catalog/catalog.jsp; Unknown Publication date but believed to be prior to present application filing date.
"Medline Catalog", CURAD Comfort Fabric Bandages; *Medline Catalog*; http://www.medline.com/catalog/catalog.jsp; Unknown Publication date but believed to be prior to present application filing date.
"Medline Catalog", CURAD Cotton Bandage Roll; *Medline Catalog*; http://www.medline.com/catalog/catalog.jsp; Unknown Publication date but believed to be prior to present application filing date.
"Medline Catalog", CURAD Cupcake Cover Bandages; *Medline Catalog*; http://www.medline.com/catalog/catalog.jsp; Unknown Publication date but believed to be prior to present application filing date.
"Medline Catalog", CURAD Dazzle Adhesive Bandage; *Medline Catalog*; http://www.medline.com/catalog/catalog.jsp; Unknown Publication date but believed to be prior to present application filing date.
"Medline Catalog", CURAD Extra Stength Waterproof Bandages; *Medline Catalog*; http://www.medline.com/catalog/catalog.jsp; Unknown Publication date but believed to be prior to present application filing date.
"Medline Catalog", CURAD Extreme Hold Bandages; *Medline Catalog*; http://www.medline.com/catalog/catalog.jsp; Unknown Publication date but believed to be prior to present application filing date.
"Medline Catalog", CURAD Eye Patch; *Medline Catalog*; http://www.medline.com/catalog/catalog.jsp; Unknown Publication date but believed to be prior to present application filing date.
"Medline Catalog", CURAD First Aid Kits; *Medline Catalog*; http://www.medline.com/catalog/catalog.jsp; Unknown Publication date but believed to be prior to present application filing date.
"Medline Catalog", CURAD Flex-Fabric Bandages; *Medline Catalog*; http://www.medline.com/catalog/catalog.jsp; Unknown Publication date but believed to be prior to present application filing date.
"Medline Catalog", CURAD Food Service Adhesive Bandages; *Medline Catalog*; http://www.medline.com/catalog/catalog.jsp; Unknown Publication date but believed to be prior to present application filing date.
"Medline Catalog", CURAD Hold Tite Tubular Stretch Bandage; *Medline Catalog*; http://www.medline.com/catalog/catalog.jsp; Unknown Publication date but believed to be prior to present application filing date.
"Medline Catalog", CURAD Knee and Elbow Bandages; *Medline Catalog*; http://www.medline.com/catalog/catalog.jsp; Unknown Publication date but believed to be prior to present application filing date.
"Medline Catalog", CURAD Mediplast Wart Pads; *Medline Catalog*; http://www.medline.com/catalog/catalog.jsp; Unknown Publication date but believed to be prior to present application filing date.
"Medline Catalog", CURAD Performance Series Antibacterial Bandages; *Medline Catalog*; http://www.medline.com/catalog/catalog.jsp; Unknown Publication date but believed to be prior to present application filing date.
"Medline Catalog", CURAD Pirates Bandages; *Medline Catalog*; http://www.medline.com/catalog/catalog.jsp; Unknown Publication date but believed to be prior to present application filing date.
"Medline Catalog", CURAD Plastic Adhesive Bandages; *Medline Catalog*; http://www.medline.com/catalog/catalog.jsp; Unknown Publication date but believed to be prior to present application filing date.
"Medline Catalog", CURAD Pressure Adhesive Bandages; *Medline Catalog*; http://www.medline.com/catalog/catalog.jsp; Unknown Publication date but believed to be prior to present application filing date.
"Medline Catalog", CURAD Self Adherent Wrap; *Medline Catalog*; http://www.medline.com/catalog/catalog.jsp; Unknown Publication date but believed to be prior to present application filing date.

(56) References Cited

OTHER PUBLICATIONS

"Medline Catalog", CURAD Sensitive Skin Bandages; *Medline Catalog*; http://www.medline.com/catalog/catalog.jsp; Unknown Publication date but believed to be prior to present application filing date.
"Medline Catalog", CURAD Silicone Flexible Fabric Bandages; *Medline Catalog*; http://www.medline.com/catalog/catalog.jsp; Unknown Publication date but believed to be prior to present application filing date.
"Medline Catalog", CURAD XL Plastic Adhesive Bandages; *Medline Catalog*; http://www.medline.com/catalog/catalog.jsp; Unknown Publication date but believed to be prior to present application filing date.
"Medline Catalog", Dora the Explorer Adhesive Bandages by Johnson & Johnson; *Medline Catalog*; http://www.medline.com/catalog/catalog.jsp; Unknown Publication date but believed to be prior to present application filing date.
"Medline Catalog", CURAD Elastic Nets; *Medline Catalog*; http://www.medline.com/catalog/catalog.jsp; Unknown Publication date but believed to be prior to present application filing date.
"Medline Catalog", First Aid Kids by Graham-Field; *Medline Catalog*; http://www.medline.com/catalog/catalog.jsp; Unknown Publication date but believed to be prior to present application filing date.
"Medline Catalog", Fourlex Bandage System; *Medline Catalog*; http://www.medline.com/catalog/catalog.jsp; Unknown Publication date but believed to be prior to present application filing date.
"Medline Catalog", Herbie the Dinosaur Bandages by Derma Sciences; *Medline Catalog*; http://www.medline.com/catalog/catalog.jsp; Unknown Publication date but believed to be prior to present application filing date.
"Medline Catalog", Latex Finger Cot by Tech-Med Services; *Medline Catalog*; http://www.medline.com/catalog/catalog.jsp; Unknown Publication date but believed to be prior to present application filing date.
"Medline Catalog", Looney Tunes Bandages by Derma Sciences; *Medline Catalog*; http://www.medline.com/catalog/catalog.jsp; Unknown Publication date but believed to be prior to present application filing date.
"Medline Catalog", Medigrip Tubular Bandages; *Medline Catalog*; http://www.medline.com/catalog/catalog.jsp; Unknown Publication date but believed to be prior to present application filing date.
"Medline Catalog", Nexcare Comfort Pals Bandages by 3M Healthcare; *Medline Catalog*; http://www.medline.com/catalog/catalog.jsp; Unknown Publication date but believed to be prior to present application filing date.
"Medline Catalog", Non-Sterile Gauze Sponges by Dynarex Corporation; *Medline Catalog*; http://www.medline.com/catalog/catalog.jsp; Unknown Publication date but believed to be prior to present application filing date.
"Medline Catalog", Non-Woven Sponges by Dynarex Corporation; *Medline Catalog*; http://www.medline.com/catalog/catalog.jsp; Unknown Publication date but believed to be prior to present application filing date.
"Medline Catalog", Ortho Glass Wraps by BSN Medical; *Medline Catalog*; http://www.medline.com/catalog/catalog.jsp; Unknown Publication date but believed to be prior to present application filing date.
"Medline Catalog", OrthoFlex Elastic Plaster of Paris Bandages by BSN Medical; *Medline Catalog*; http://www.medline.com/catalog/catalog.jsp; Unknown Publication date but believed to be prior to present application filing date.
"Medline Catalog", Planets & Stars Adhesive Bandages by Derma Sciences; *Medline Catalog*; http://www.medline.com/catalog/catalog.jsp; Unknown Publication date but believed to be prior to present application filing date.
"Medline Catalog", Pre-Cut Tubular Bandages by Medical Action; *Medline Catalog*; http://www.medline.com/catalog/catalog.jsp; Unknown Publication date but believed to be prior to present application filing date.
"Medline Catalog", Reinforced Waterproof Bandges by ASO Corp; *Medline Catalog*; http://www.medline.com/catalog/catalog.jsp; Unknown Publication date but believed to be prior to present application filing date.
"Medline Catalog", Scooby Doo Bandages by Derma Sciences; *Medline Catalog*; http://www.medline.com/catalog/catalog.jsp; Unknown Publication date but believed to be prior to present application filing date.
"Medline Catalog", Spiderman Bandages by Derma Sciences; *Medline Catalog*; http://www.medline.com/catalog/catalog.jsp; Unknown Publication date but believed to be prior to present application filing date.
"Medline Catalog", SpongeBob SquarePants Adhesive Bandages by Jonson & Johnson; *Medline Catalog*; http://www.medline.com/catalog/catalog.jsp; Unknown Publication date but believed to be prior to present application filing date.
"Medline Catalog", Stat Strip Adhesive Bandages; *Medline Catalog*; http://www.medline.com/catalog/catalog.jsp; Unknown Publication date but believed to be prior to present application filing date.
"Medline Catalog", Stat Strip Bandages by Derma Sciences; *Medline Catalog*; http://www.medline.com/catalog/catalog.jsp; Unknown Publication date but believed to be prior to present application filing date.
"Medline Catalog", Sterile NonWoven Post Op Sponges by Dynarex; *Medline Catalog*; http://www.medline.com/catalog/catalog.jsp; Unknown Publication date but believed to be prior to present application filing date.
"Medline Catalog", Stocked First Aid Kit—50 Person by Graham-Field; *Medline Catalog*; http://www.medline.com/catalog/catalog.jsp; Unknown Publication date but believed to be prior to present application filing date.
"Medline Catalog", Tubigrip by Alimed; *Medline Catalog*; http://www.medline.com/catalog/catalog.jsp; Unknown Publication date but believed to be prior to present application filing date.
"Medline Catalog", Tubigrip Elasticated Tubular Bandages by Molnlyke; *Medline Catalog*; http://www.medline.com/catalog/catalog.jsp; Unknown Publication date but believed to be prior to present application filing date.
"Medline Catalog", Unna-Z Unna Boot Bandages; *Medline Catalog*; http://www.medline.com/catalog/catalog.jsp; Unknown Publication date but believed to be prior to present application filing date.
"Medline Catalog", Vetrap Bandaing Tapes by 3M Healthcare; *Medline Catalog*; http://www.medline.com/catalog/catalog.jsp; Unknown Publication date but believed to be prior to present application filing date.
Hofsass, Jeffery A., "NonFinal OA", U.S. Appl. No. 14/445,749, filed Jul. 29, 2014; Mailed Sep. 22, 2015.
Frank, Keith "Notice of Allowance", U.S. Appl. No. 29/497,852, filed Jul. 29, 2014; Oct. 1, 2015.
Hofsass, Jeffery "Notice of Allowance", U.S. Appl. No. 14/445,749; filed Jul. 29, 2014; Mailed Jan. 22, 2016.

\* cited by examiner

FIRST AID KIT WITH SPEECH, MUSIC, OR INSTRUCTIONAL SOUND EMISSION

BACKGROUND

1. Technical Field

This disclosure relates generally to containers, and more particularly to first aid kits.

2. Background Art

Nicks, cuts, and scrapes are a common hazard. In many cases, when a person injures himself or herself, the most efficient way to heal the injury is by retrieving medical supplies from a first aid kit. Most household first aid kits include implements for cleaning the wound, applying an antibiotic or other treatment, and then covering the wound with a bandage. While this process works well to heal the wound, it is not perfect. Some users, including younger users, may not know how to use the materials within the first aid kit. Even older users may be unfamiliar with new medical devices, such as novel bandages, wound treatments, cleaning implements, and so forth. Additionally, convincing some users to use, or properly use, a first aid kit can be difficult. Where a wound needs treatment and an injured person fails to treat the wound, bacteria or other microbes may enter the wound and cause an infection.

Figure 1:
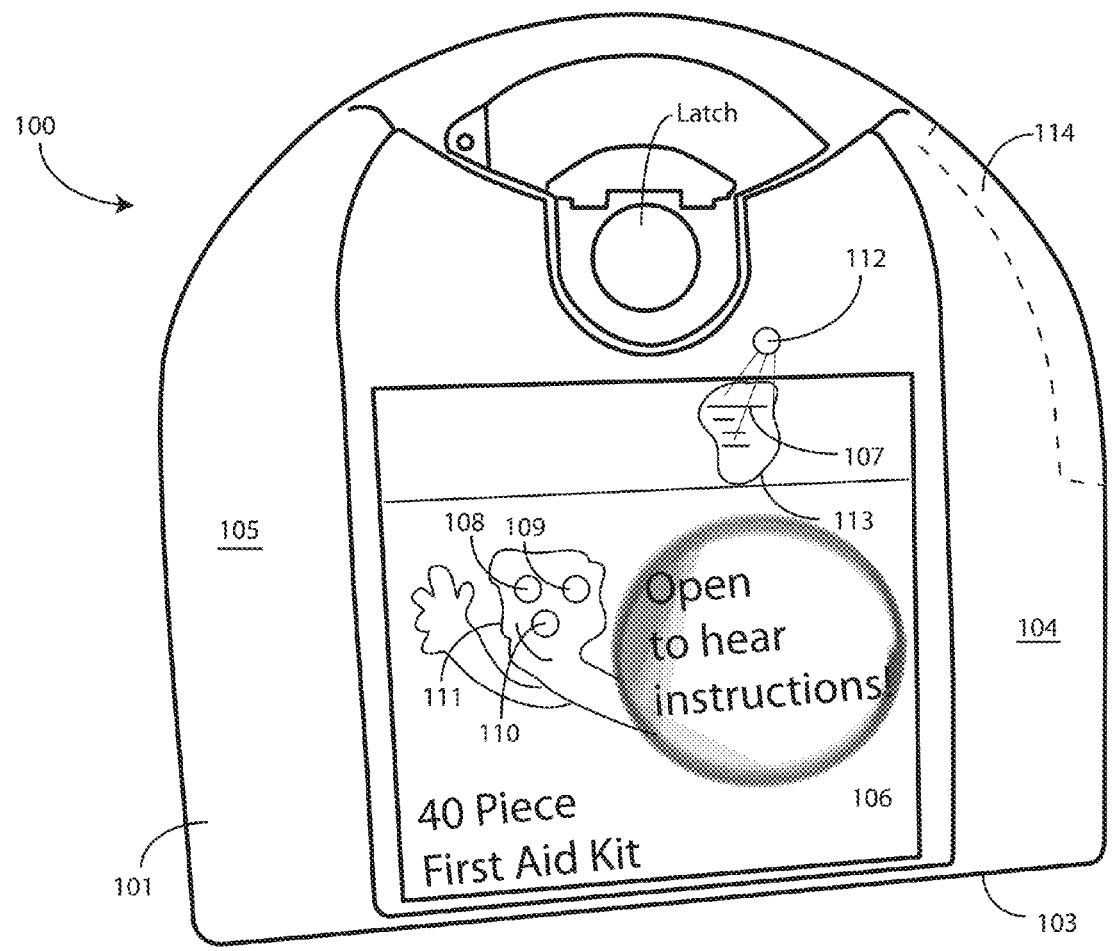
FIG. 1 illustrates one explanatory container configured in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

It will be appreciated that embodiments of the disclosure described herein may be comprised of one or more conventional processors and unique stored program instructions that control the one or more processors to implement, in conjunction with certain non-processor circuits, some, most, or all of the functions of sound emission from a container as described herein. The non-processor circuits may include, but are not limited to, acoustic drivers, signal amplifiers, signal drivers, clock circuits, power source circuits, and user input devices. As such, these functions may be interpreted as steps of a method to perform sound emission from a container as described below. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

As noted above, many people who injure themselves are reluctant to use a first aid kit. In some cases, they may simply not want to take the time to use the first aid kit. In other cases, they may not know how to use the contents of a first aid kit to treat a wound. Younger users, including children, may find first aid kits "scary" in that they connote images of trips to the doctor where shots or stitches were received. Each of these conditions can result in an untreated wound that gets infected or worse.

Embodiments of the disclosure provide a container that in one embodiment, when a first container body part is opened relative to a second container body part, emits sound. In other embodiments, lifting the container off a table or other flat surface can cause the container to emit sound. In still other embodiments, unlatching a lock holding the first container body part and the second container body part together can cause sound emission. Regardless of what action is used to actuate a sensor, the resulting emitted sound can be, in one embodiment, entertaining so as to entice a user to more regularly use the container, which is configured as a first aid kit in one or more embodiments. Alternatively, the sound can be speech, such as that from a popular character on a television show, or movie. In one embodiment, the emitted sound comprises one or more instructions on how to use first aid items stored within the container such as bandages, dressings, sutures, antiseptics, and so forth. For example, in one embodiment a sensor is configured to determine which item is removed from the container. The sensor is then configured to cause a sounder to emit sound with instructions identifying the item, explaining how to use the item, or combinations thereof. Of course, combinations of music, speech, and instructional material can be used as the emitted sound as well.

Illustrating by example, in one embodiment a container is configured as a first aid kit for use when children are injured. Accordingly, when the first container body part is opened relative to a second container body part, music may play to stimulate the child's interest and/or provide comforting sensations to a child that has been injured. While or after this music is playing, a familiar voice, such as that from a popular cartoon or children's show, may deliver speech. For instance, the character might say, "Hello there, Buster! Did you hurt yourself? You look like you could use a bandage. You may want to clean that boo-boo first to make sure it doesn't get infected!"

In one embodiment, a sensor is capable of determining which first aid item a user draws from the container. Thus, if the user retrieves a bandage prior to an antiseptic dressing, the character might say, "That's a bandage. Don't you want to get the antiseptic wipe first? Its best to clean the boo-boo first."

After this, instructional material may be delivered. The character might say, "First, make sure your skin is clean and dry. Then apply the bandage so that the sticky stuff attaches to your skin with the white pad over your boo-boo. And remember, put on a new bandage every day, or more frequently if it gets wet. I want you to feel better soon!" In another embodiment, a container can be configured for adults or people of all ages.

In one embodiment, to make the container more fun to use, while at the same time preserving the sterility of first aid items stored therein, the container can include two container body parts. The two container body parts can include a latch to retain them together until they are used. The two container body parts can encloses a first aid item receiving cavity having one or more first aid items stowed therein. In one embodiment, the sound emission is triggered when the second first container body part opens relative to the first container body part.

In another embodiment, the sensor detects the container being lifted from a flat surface, such as a table. For example, in one embodiment when a user picks up the container, a pressure-sensing sensor detects this and causes the sounder to emit sound. The sounder may say, "Uh oh, did you hurt yourself? I sure am glad you are using a first aid kit. Open the lid to learn how to use the implements inside." Advantageously, this embodiment that causes the sounder to emit sound when being picked up—and not opened—allows a curious youngster to play with a first aid kit and hear fun, interesting, and educational sounds without damaging or contaminating the first aid items held within the receiving cavity of the container.

Also advantageously, this embodiment allows consumers to "demo" the container in the store to determine whether the particular sounds emitted by the container are suitable for their needs. For example, a manufacturer may offer several different containers, each emitting a different type of sound. One may be particularly well suited for boys, while another is particularly well suited for girls. A boy's mother may prefer a sound stating, "Hey there, did you get hurt playing football?" over one that says, "Does your dolly need a bandage too?" By allowing the mother to test the sound emission without opening the container in the store, she is able to confidently select the most appropriate package for her child.

In one embodiment where two container body parts are used, the first container body part is initially sealed to the second container body part with a tamper-proof seal. As noted in the preceding paragraph, in some embodiments a person can try the sound-emission in a store prior to purchase. By sealing the first container body part to the second container body part with a tamper-proof seal, a subsequent purchaser is assured that the first aid items disposed within the receiving cavity still have the manufacturer's original integrity and sterility.

Figure 2:
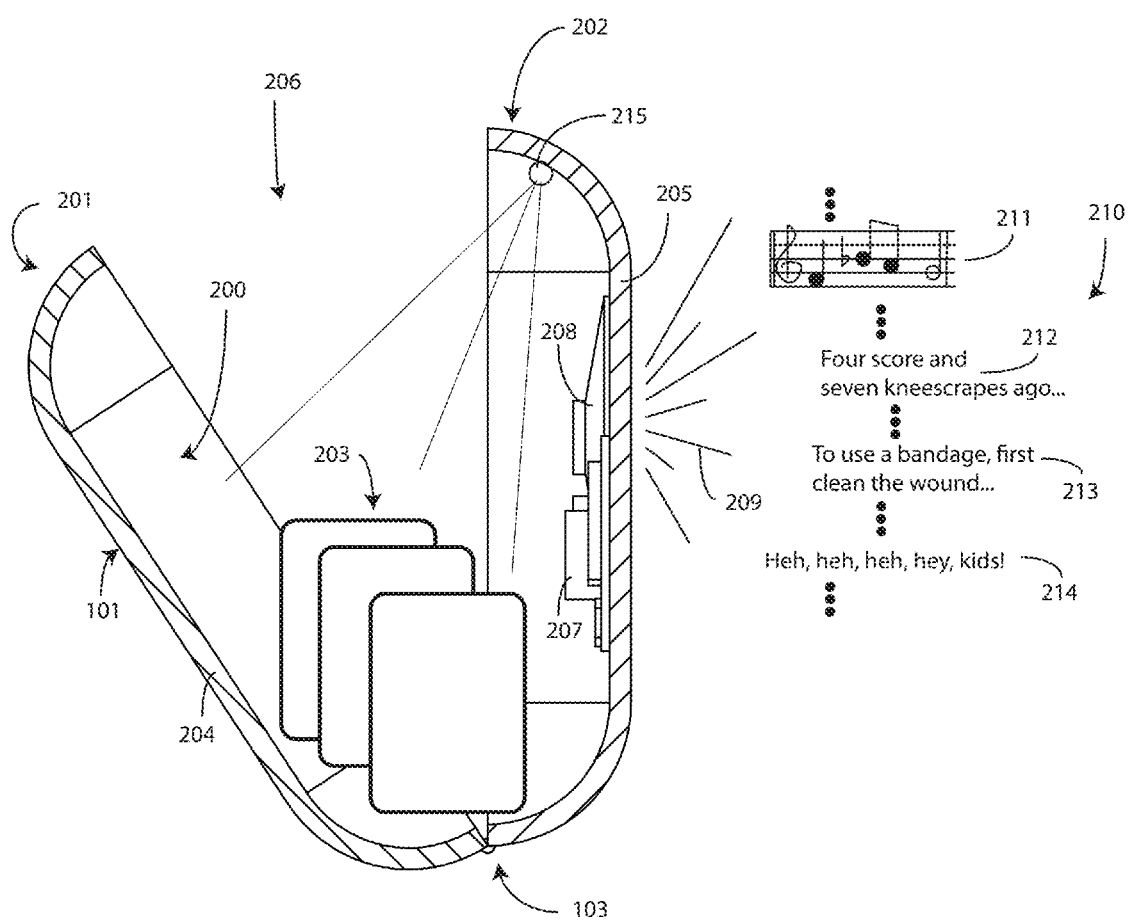
FIG. 2 illustrates one explanatory container in an open configuration in accordance with one or more embodiments of the disclosure.

Turning now to FIGS. 1 and 2, illustrated therein is one embodiment of a container 100 configured in accordance with one or more embodiments of the disclosure. FIG. 1 illustrates a perspective view of one explanatory container 100, while FIG. 2 illustrates a sectional view of portions of the container helpful in understanding the operation of one or more embodiments of the container 100.

In one embodiment, the container 100 is configured as a first aid kit. This configuration will be used in the description below for explanatory purposes. However, it should be noted that the container 100 could be configured in other ways, such as to contain school supplies, art supplies, cooking supplies, or any other type of implements. Still other configurations will be obvious to those of ordinary skill in the art having the benefit of this disclosure.

The container 100 of FIGS. 1 and 2 includes a container body 101 that includes a base 103 and a plurality of sidewalls 104,105,204,205. In one embodiment the plurality of sidewalls 104,105,204,205 extend distally from the base 103 and define a receiving cavity 200 to receive one or more first aid items 203.

In one embodiment, the container body 101 includes a first container body part 201 and a second container body part 202. In FIG. 1, the first container body part (201) and the second container body part (202) are in a closed position. By contrast, in FIG. 2 one of the first container body part 201 or the second container body part 202 has pivoted from the closed position of FIG. 1 to a radially displaced open position revealing the one or more first aid items 203. An optional seal (114), such as tape or plastic, can be provided to retain the first container body part (201) in the closed position until the seal (114) is broken. When the first container body part 201 or the second container body part 202 pivots to the radially displaced open position relative to the other container body part, an opening 206 of the receiving cavity 200 is created as shown in FIG. 2.

In this illustrative embodiment, the first container body part 201 is pivotally coupled to the second container body part 202. While a pivotally coupled first container body part will be used herein for illustrative purposes, due to its ease of construction, it should be noted that the first container body part 201 could take any of a number of other configurations relative to the second container body part 202 as well. For example, the first container body part 201 could be removable from the second container body part 202. The first container body part 201 could screw, snap, or otherwise attach—and be removable from—the second container body part 202 in one embodiment. In another embodiment, the first container body part 201 could be tethered to the second container body part 202 so as to be separable from, but retained to, the second container body part 202. Other forms of first container body part/second container body part configurations will be obvious to those of ordinary skill in the art having the benefit of this disclosure.

In this illustrative embodiment, the first container body part 201 is configured to pivot from a closed position enclosing the one or more first aid items 203 in the receiving cavity 200, as shown in FIG. 1, and a radially displaced open position revealing the one or more first aid items 203 through the opening 206 as shown in FIG. 2. It should be noted that the first container body part 201 can be rotated relative to the second container body part 202, or vice versa. Additionally, the first container body part 201 and second container body part 202 can pivot relative to teach other. In this illustrative embodiment, pivoting the first container body part 201 to the radially displaced open position reveals not only the receiving cavity 200 and its opening 206, but the one or more first aid items 203 disposed within the receiving cavity 200 as well.

As will be illustrated in more detail below, in this illustrative embodiment the container 100 includes a sensor 207 to detect one of the first container body part 201 or the second container body part 202 in—or transitioning to—the radially displaced open position. The sensor 207 is operable with a sounder 208, which is something capable of producing audible sound 209. When the sensor detects that one of the first container body part 201 or the second container body part 202 is in, or alternatively is transitioning to, the radially displaced open position relative to the other, the sounder 208 can emit the audible sound 209.

In one embodiment, this emission of audible sound 209 comprises emitting one or more pre-recorded sounds 210. Examples of the one or more pre-recorded sounds 210 include music 211, speech 212, instructional materials 213, amusing and fanciful utterances 214, or combinations thereof. Accordingly, whenever a user opens the container 100 by pivoting one of the first container body part 201 or the second container body part 202 to the radially displaced open position, not only are they able to remove one of the one or more first aid items 203 from the container, but they are entertained, enlightened, informed and/or amused in the process.

In one embodiment, the container 100 includes a token 106 indicating that the container 100 is configured for the emission of audible sound 209. As used herein, a "token" takes the principal meaning from the dictionary, which is that of "a think serving as a visible or tangible representation of a fact or quality." Thus, in one embodiment, the token 106 comprises indicia stating, "Open the first container body part and this box speaks!" or "Open to hear instructions!"

In another embodiment, the token 106 is suggestive in nature. As an example, it may ask a rhetorical question that invites a user to manipulate the container 100 as follows: "Ever hear a first aid kit talk, buddy?" In another embodiment, the token 106 comprises a fanciful announcement providing an indication of the container's capabilities. For example, the token 106 may state, "Open the kitty to hear me talk." These tokens are illustrative only, as others will be obvious to those of ordinary skill in the art having the benefit of this disclosure.

As noted, the audible sound 209 can take a variety of forms. In one embodiment, the audible sound 209 comprises music 211. The music 211 may comprise background music over which speech 212, instructional materials 213, or fanciful utterances 214 are recorded. In another embodiment, the music 211 comprises front music that includes no speech, lyrics, or words. The delivery of music 211 is advantageously effective in at least two ways: First, it entices a user to actually use the container 100 by providing an entertaining experience while the user retrieves a bandage, salve, topical ointment, cleansing wipe, or other first aid item 203.

Second, the emission of music 211 provides a calming experience that can be especially useful when a person in need of a first aid is injured. This is particularly true when that person is a child. Embodiments of the disclosure contemplate that people in general, and particularly frightened children, find comfort in music and fanciful characters. Music can be used in therapy to help with various issues, such as hyperactivity, temper tantrums, staying quiet and relaxed, and nightmares. Music can also be used in dealing with stress, trauma, or injury. In basic terms, music provides a comforting user experience. For this reason, in one embodiment, when the sensor detects one of the first container body part 201 or the second container body part 202 in or transitioning to the radially displaced open position, the sounder 208 is to emit music 211.

In another embodiment, the sounder 208 can be configured to emit speech 212 when the sensor detects one or both of the first container body part 201 or the second container body part 202 in or transitioning to the radially displaced open position. Examples of speech emissions include comforting slogans, poems, soothing narratives, words of encouragement, get well wishes, expressions of sympathy, expressions of empathy, therapeutic statements to reduce pain, and motivational soliloquys. Other types of speech 212 will be obvious to those of ordinary skill in the art having the benefit of this disclosure.

In another embodiment, the sounder 208 can be configured to emit instructional material 213 when the sensor detects one of the first container body part 201 or the second container body part 202 in or transitioning to the radially displaced open position. Alternatively, as will be described below with reference to FIG. 3, in one embodiment the sensor 207 is capable of determining which first aid item 203 is being selected, retrieved, and/or withdrawn from the container 100 by a user. Where this happens, the sounder 208 can be configured to emit an identification of the item, instructions for using the item, combinations thereof, or other information about the item. In one embodiment the instructional materials 213 comprises instructions for using one or more of the container 100 or the one or more first aid items 203 disposed within the container 100.

In one embodiment the container 100 includes instructional material, warnings, and/or health care suggestions 107 disposed on an exterior of one sidewall. Embodiments of the disclosure contemplate that users are sometimes reluctant to take the time to read such instructional material, warnings, and/or health care suggestions 107. Thus, in one embodiment, the instructional materials 213 emitted by the sounder comprises a reading of the instructional material, warnings, and/or health care suggestions 107 to ensure that the instructional material, warnings, and/or health care suggestions 107 are delivered to the user. The instructional materials 213 emitted by the sounder may say, "Use this first aid kit when you are injured. For example, if you have a cut, reach inside the first aid kit, retrieve a bandage, and apply the bandage to clean, dry skin. Change bandage daily or when pad becomes wet," in one embodiment.

In another embodiment, the instructional materials 213 may be supplemental to any instructional material, warnings, or health care suggestions 107 disposed along the container 100. For example, the instructional materials 213 emitted by the sounder may say, "For medical emergencies, please seek professional help or call 911." In another embodiment, the instructional materials 213 emitted by the sounder 208 may say, "In case of deep or puncture wounds, or serious burns, consult a physician or call 911." In another embodiment, the instructional materials 213 emitted by the sounder may say, "If irritation or redness develops or persists, discontinue use and consult your healthcare provider or go quickly to the emergency room." Of course, combinations of these can be used. Moreover, other forms of instructional materials 213 suitable for emission by the sounder when the sensor detects one of the first container body part 201 or the second container body part 202 in or transitioning to the radially displaced open position will be obvious to those of ordinary skill in the art having the benefit of this disclosure.

In another embodiment, the sounder 208 can be configured to emit fanciful utterances 214 when the sensor detects one of the first container body part 201 or the second container body part 202 in or transitioning to the radially displaced open position. Examples of fanciful utterances 214 include catch phrases of famous characters, such as "Elementary, my dear Watson," which is the catch phrase of the famous character Sherlock Holmes. Another example of a fanciful utterance 214 would be modifications of tag lines or well-known phrases to make the fanciful utterance 214 more suited for use with the container 100. For example, rather than Santa Claus saying, "Ho ho ho . . . " the fanciful utterance 214 may comprise Santa Claus saying, "Ho ho Noooo!" or "Ho ho oh no!!! Use a first aid kit!" to provide a fanciful utterance 214 that provides a commiserating user experience. Other fanciful utterances 214 will be obvious to those of ordinary skill in the art having the benefit of this disclosure.

In one embodiment, the container 100 optionally includes one or more lights 108,109,110. The one or more lights 108,109,110 can be operable with the sensor 207 to illuminate, flash, or otherwise emit light when the sensor 207 detects that one of the first container body part 201 or the second container body part 202 is in—or transitioning to—the radially displaced open position. The inclusion of one or more lights 108,109,110 can provide an even more entertaining, informative, or inviting user experience.

In one embodiment, the one or more lights 108,109,110 form features of a character or fanciful character. For example, in the illustrative embodiment of FIG. 1, the one or more lights 108,109,110 for the eyes and nose of a fanciful character 111 printed on a sidewall of the container 100. The one or more lights 108,109,110 can be used in other ways as well. For instance, in one embodiment the one or more lights 108,109,110 can be configured as fireworks that provide a visual appearance of being launched in the air when one of the first container body part 201 or the second container body part 202 is pivoted to the radially displaced open position. Other configurations of one or more lights 108,109,110 will be obvious to those of ordinary skill in the art having the benefit of this disclosure.

In one embodiment, one or more lights can be used to illuminate to highlight, when actuated by the sensor, one or more of a predefined area of an exterior of the container 100 or a predefined area of an interior of the receiving cavity 200. Illustrating by example, light 112 is used to highlight the instructional material, warnings, and/or health care suggestions 107, which are disposed on a predefined area 113 of the exterior of the container 100. Similarly, light 215 could be used to highlight the interior of the receiving cavity 200, thus making it easier for a user to see the one or more first aid items 203 in low-light environments.

In one embodiment, one or more lights can be used to illuminate to highlight, when actuated by the sensor, one or more instructions or illustrations disposed along the container 100 while the sounder emits the one or more pre-recorded sounds 210. For example, where the instructional material, warnings, and/or health care suggestions 107 comprise instructions, and the pre-recorded sounds 210 comprise instructional materials 213 that reads the instructions, the instructions can be highlighted by light 112 while the instructional materials 213 reads the instructions for using one or more of the container 100 or the one or more first aid items 203 disposed within the receiving cavity 200. Other applications for lights will be obvious to those of ordinary skill in the art having the benefit of this disclosure.

Figure 3:
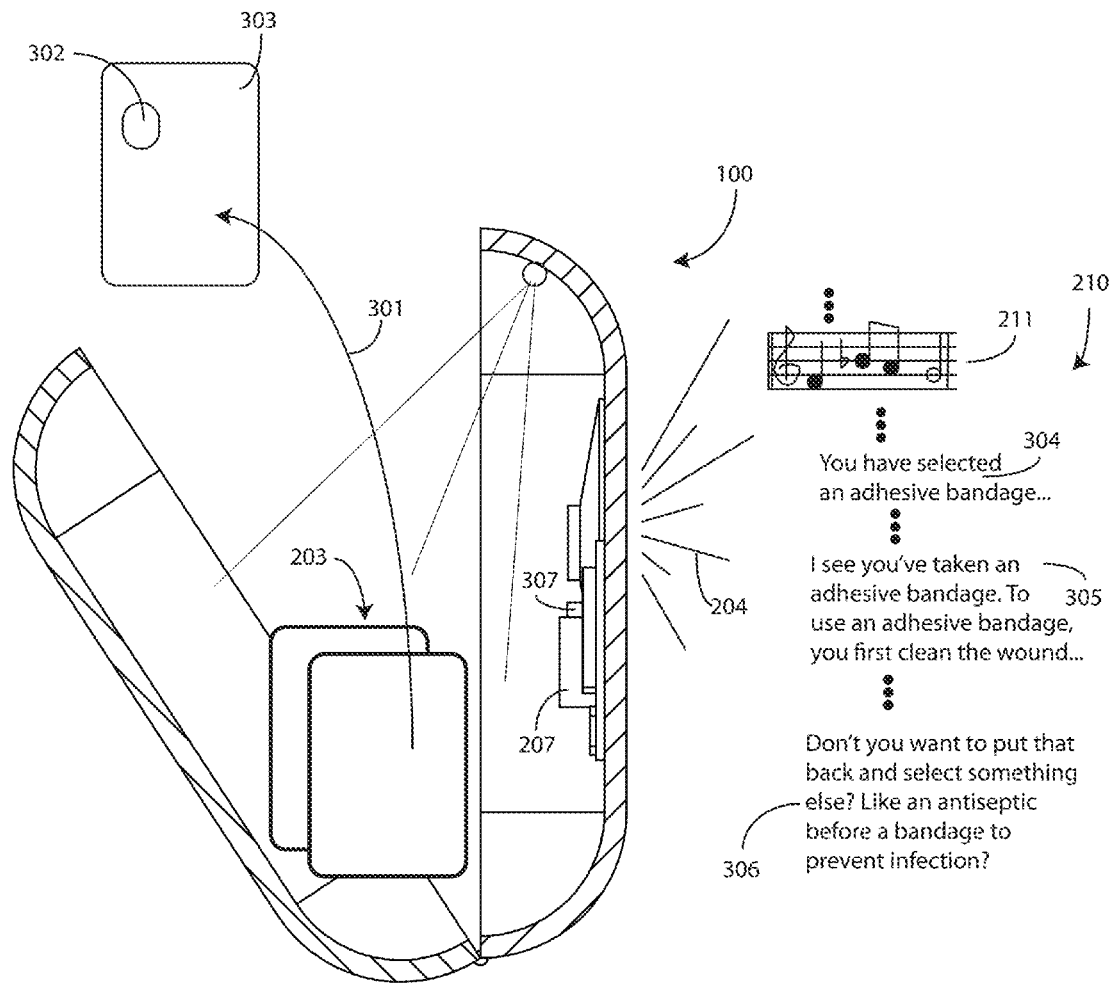
FIG. 3 illustrates one explanatory container being used in accordance with a method of one or more embodiments of the disclosure.

Turning now to FIG. 3, in one embodiment the sensor 207 further detects removal 301 of at least one first aid item 303 from the container 100. The sensor 207 can also be configured to identify the at least one first aid item 303 removed 301 from the container 100. For example, each item may be tagged with a Radio Frequency Identification (RFID) tag 302 in one or more embodiments. The sensor 207 could be equipped with an RFID reader 307. When the at least one first aid item 303 is removed from the container 100, the RFID reader 307 can read the RFID tag 302 to not only detect the removal 301 of the at least one first aid item 303, but also to identify the at least one first aid item 303. Accordingly, when this occurs, in one embodiment the one or more pre-recorded sounds 210 can comprise an aural identification 304 of the at least one first aid item 303, instructions 305 for using the at least one first aid item 303, or combinations thereof. Of course, this can be emitted with or without music 211.

Illustrating by example, suppose the at least one first aid item 303 is a bandage. The aural identification 303 may state, "You have selected an adhesive bandage!" The instructions 305 may state, "I see that you have selected an adhesive bandage. To use an adhesive bandage, first remove the backing paper . . . " Other aural identification 303 statements will be obvious to those of ordinary skill in the art having the benefit of this disclosure.

In one or more embodiments, where there is a recommended sequential order for using the one or more first aid items 203 and the items are not removed in accordance with their sequential order, the pre-recorded sounds 210 may comprise suggestions 306 for selecting a different first aid item. For example, if the manufacturer of the container 100 wishes for a topical ointment to be used prior to an adhesive bandage, the suggestions 306 may state, "I see you have selected a bandage. You may want to select the topical ointment first to prevent an infection. Wouldn't you rather put the bandage back and get the ointment so you don't get an infection and end up in the hospital?" Other suggestions 309 will be obvious to those of ordinary skill in the art having the benefit of this disclosure.

Figure 4:
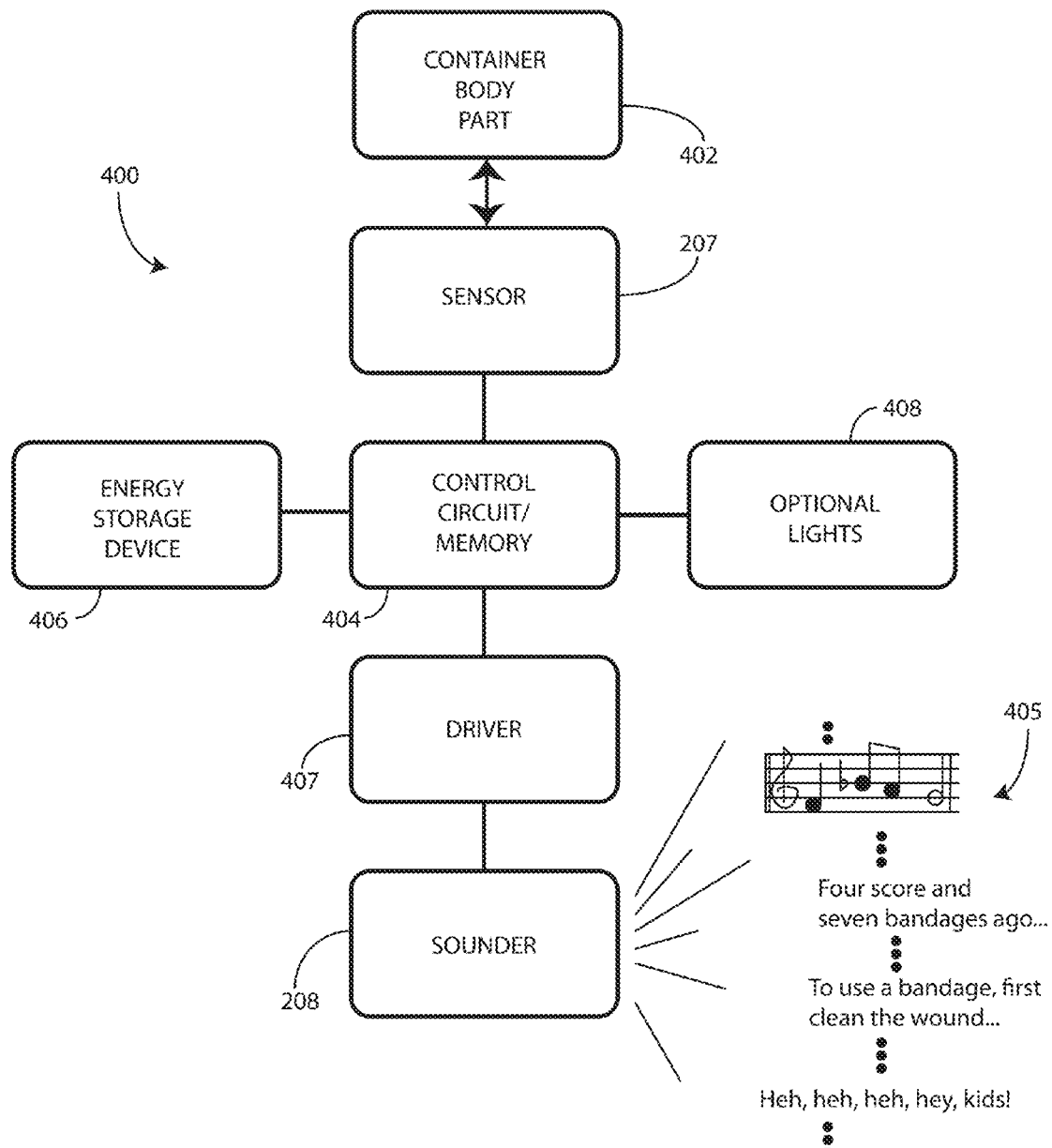
FIG. 4 illustrates a schematic block diagram of a container in accordance with one or more embodiments of the disclosure.

Turning now to FIG. 4, illustrated therein is one explanatory schematic block diagram of a sounding mechanism 400 configured in accordance with one or more embodiments of the disclosure. The illustrative sounding mechanism 400 of FIG. 4 includes the sensor 207 that is operable to detect a container body part 401 in or transitioning to an open position relative to another container body part. The sounder 208, operable with the sensor 207, is to emit one or more pre-recorded audio sounds 405 when the sensor 207 detects the container body part 401 in or transitioning to an open position as previously described. Examples of sounders include loudspeakers, piezoelectric transducers, and other acoustic transducers.

In one embodiment, one or more control circuits 404 serve as the operational hub of the sounding mechanism 400. The one or more control circuits 404 also serve as an interface between the sensor 207 and the sounder 208. The one or more control circuits 404 can include a processing circuit such as a microprocessor or programmable logic, and can be configured to be operable with the sensor 207. For instance, one or more control circuits 404, through embedded executable code or programmed logic, can be configured to actuate the sounder 208 in response to electrical signals received from the sensor 207. In one embodiment, the one or more control circuits 404 include on-board memory, or are operable with separate memory devices, which store data corresponding to recorded sound expressions. For example, the memory devices can store the pre-recorded audio sounds 405. As also noted above, the one or more control circuits 404 can include, or be operable with, an RIFD reader (307).

Where one or more control circuits 404 are used, additional features can be added as well. For example, the one or more control circuits 404 can be configured to emit the pre-recorded audio sounds 405 only for a predetermined duration or time period. The one or more control circuits 404 can also cycle through different pre-recorded audio sounds 405, in series or randomly, to provide the user with a more dynamic user experience.

An energy storage device 406, such as a lithium-ion battery, can be included to provide power to the various components. In one or more embodiments, one or more drivers 907, operable with the sounder, can amplify the pre-recorded audio sounds 405 and can deliver one or more of the recorded sound expressions to the sounder 208. As noted above with reference to FIGS. 1 and 2, one or more lights can be optionally included.

Figure 5:
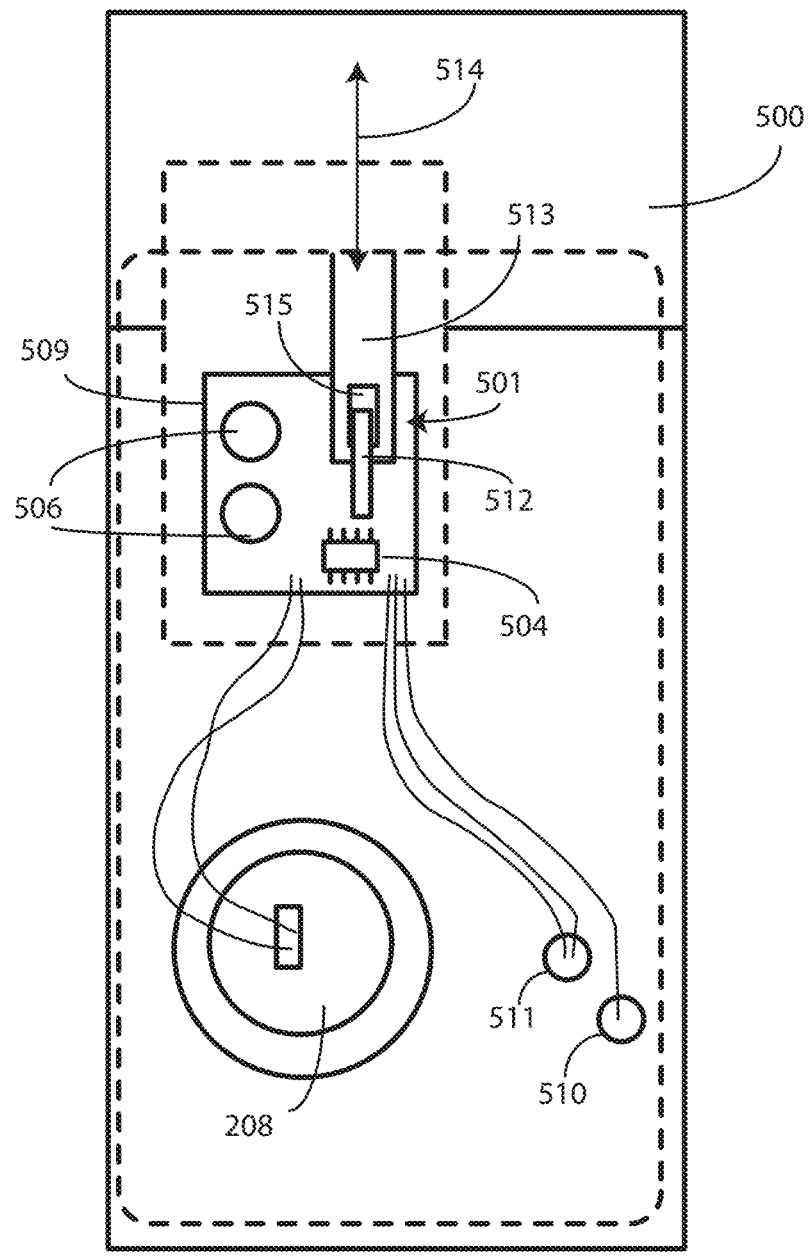
FIG. 5 illustrates one explanatory component carrier in accordance with one or more embodiments of the disclosure.

Turning now to FIG. 5, illustrated therein is one example of physical components that can be used to create a circuit corresponding to the schematic block diagram components of FIG. 4. In FIG. 5, the various components have been disposed along a carrier 500, which can be a plastic or film layer, or alternatively a section of material that is common with the container into which the components will be placed, e.g., cardboard stock.

In the illustrative embodiment of FIG. 5, a control circuit 504 is disposed on a circuit board 509, which may be a flexible printed circuit board, rigid printed circuit board, or other. The control circuit 504 includes an on-board memory device and on board drivers for the sounder 208, which in this embodiment is a cone-driven loudspeaker. Two coin size batteries 506 serve as energy storage devices for the control circuit 504 and the sensor 207. Two lights 510,511 are operable with the control circuit 504 in this embodiment as well.

In this embodiment, the sensor 207 comprises a spring contact switch 512 and an insulating slider 513. The insulating slider 513 can be coupled to one of the first container body part (201) of a container (100) or the second container body part (202) of the container (100), while the other container body part is coupled to the carrier 500. When the one of the first container body part (201) or the second container body part (202) is opened, the insulating slider 513 translates 514. This allows the spring contact switch 512 to close by contacting a conductive pad 515. This actuates the sounder 208 by delivering electrical signals to the control circuit 504. The control circuit 514 can then actuate the sounder 208 and optionally the one or more lights 510,511. An optional partition 516 can be included to divide the receiving cavity (200) into a first portion and a second portion, with the one or more first aid items (203) disposed within the first portion, the sounder 208 disposed within the second portion.

Figure 6:
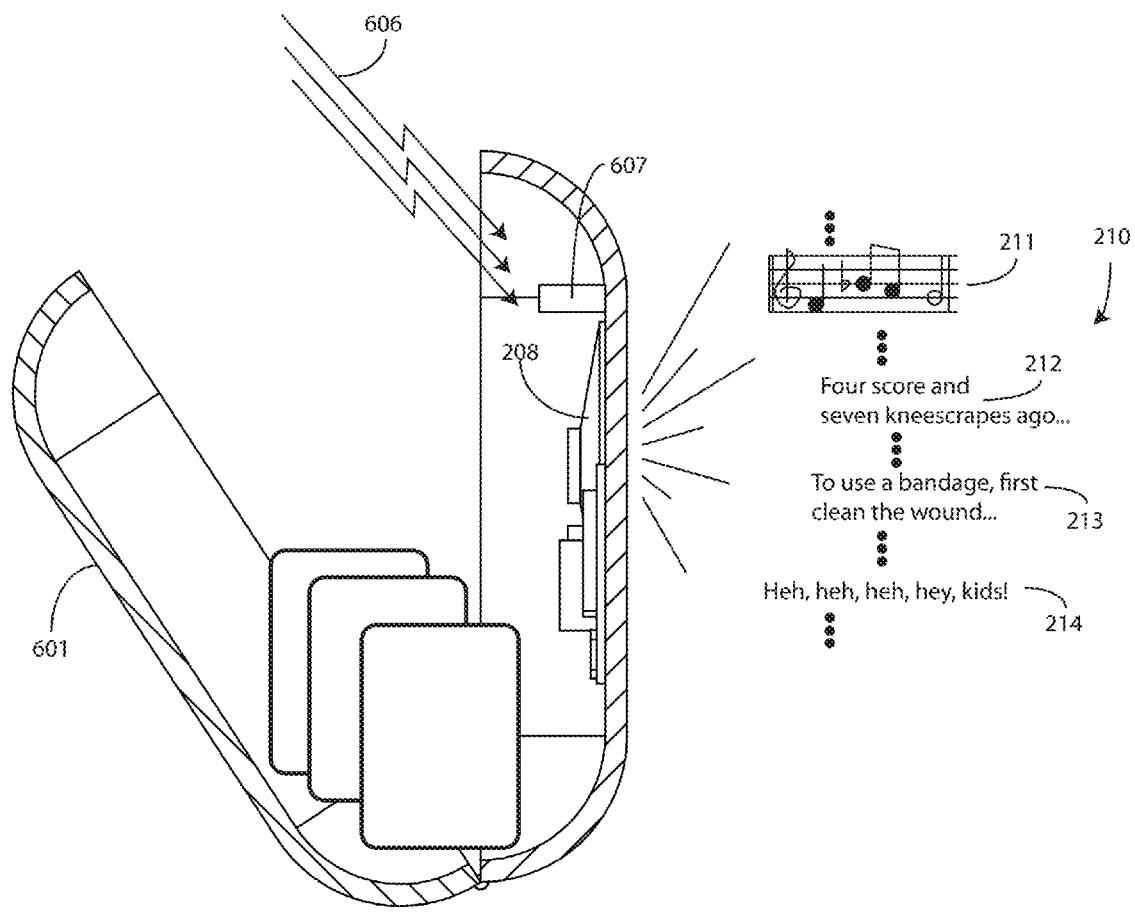
FIG. 6 illustrates another explanatory container in an open configuration in accordance with one or more embodiments of the disclosure.

A spring contact switch 512 is but one configuration of a sensor suitable for use with one or more embodiments of the disclosure. In other embodiments, a light sensor can be used as the sensor (207). Turning now to FIG. 6, illustrated therein is such an embodiment.

In FIG. 6, the sensor 607 is a light detector. The sensor 607 detects the first container body part 601 in—or transitioning to—the radially displaced open position by detecting light. The sensor 607 is operable with a sounder 208, and optionally one or more lights. When the first container body part 601 is in, or alternatively is transitioning to, the radially displaced open position, the sensor 607 receives light 606 to detect this first container body part state. The sounder 208, operable with the sensor 607, can emit the pre-recorded sound 210. In one embodiment, this emission of pre-recorded sound 210 comprises emitting one or more of music 211, speech 212, instructional materials 213, amusing and fanciful utterances 214, or combinations thereof.

Figure 7:
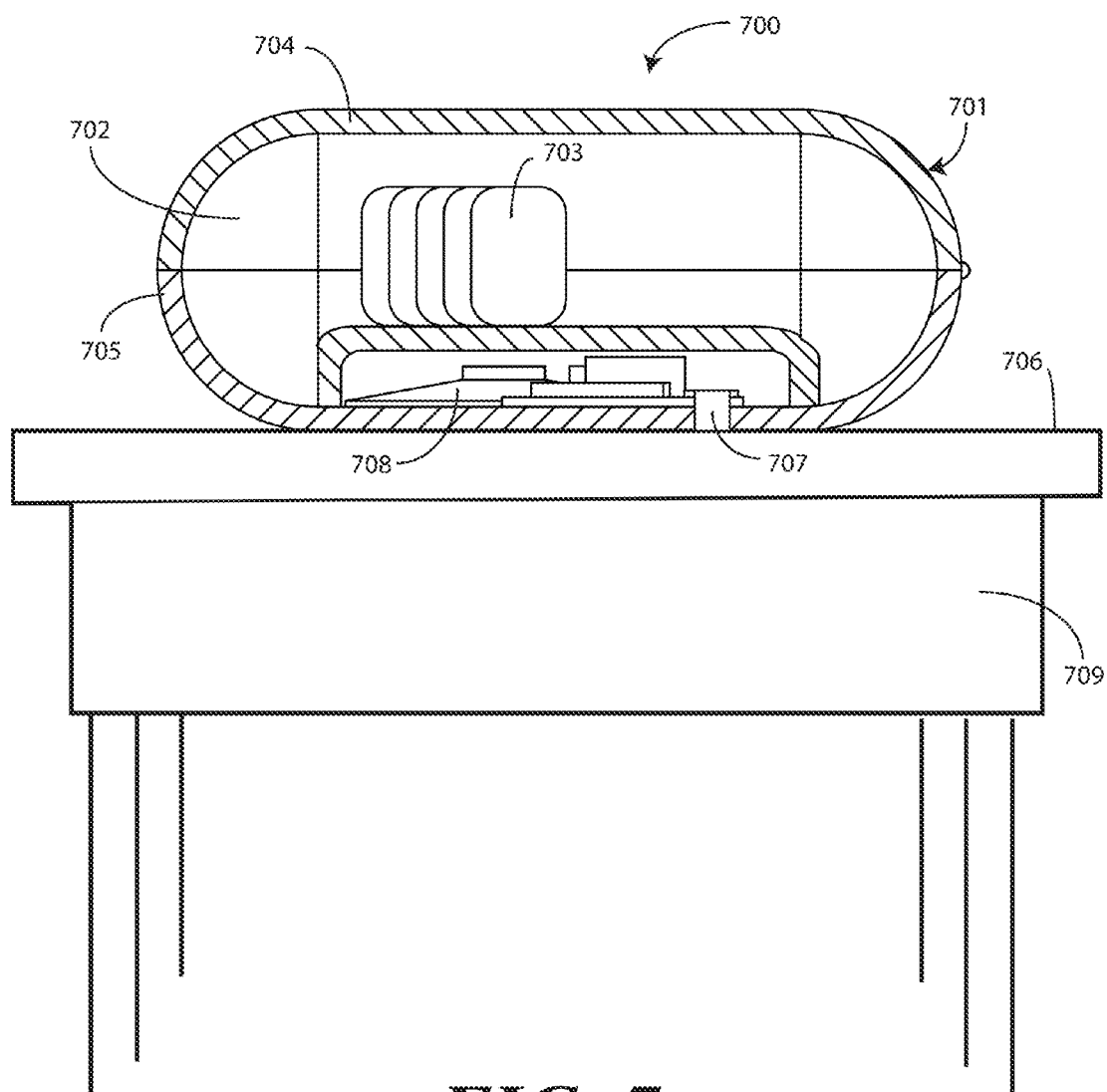
FIGS. 7 and 8 illustrate another explanatory container configured in accordance with one or more embodiments of the disclosure.

Turning now to FIG. 7, illustrated therein is an alternate container 700. The container 700 includes a container body 701 defining a receiving cavity 702 to receive one or more first aid items 703. As with previous embodiment, the container body 701 comprises a first container body part 704 and a second container body part 705. The first container body part 704 is to transition between a closed position enclosing the one or more first aid items 703 and an open position revealing the one or first aid items 703.

Figure 8:
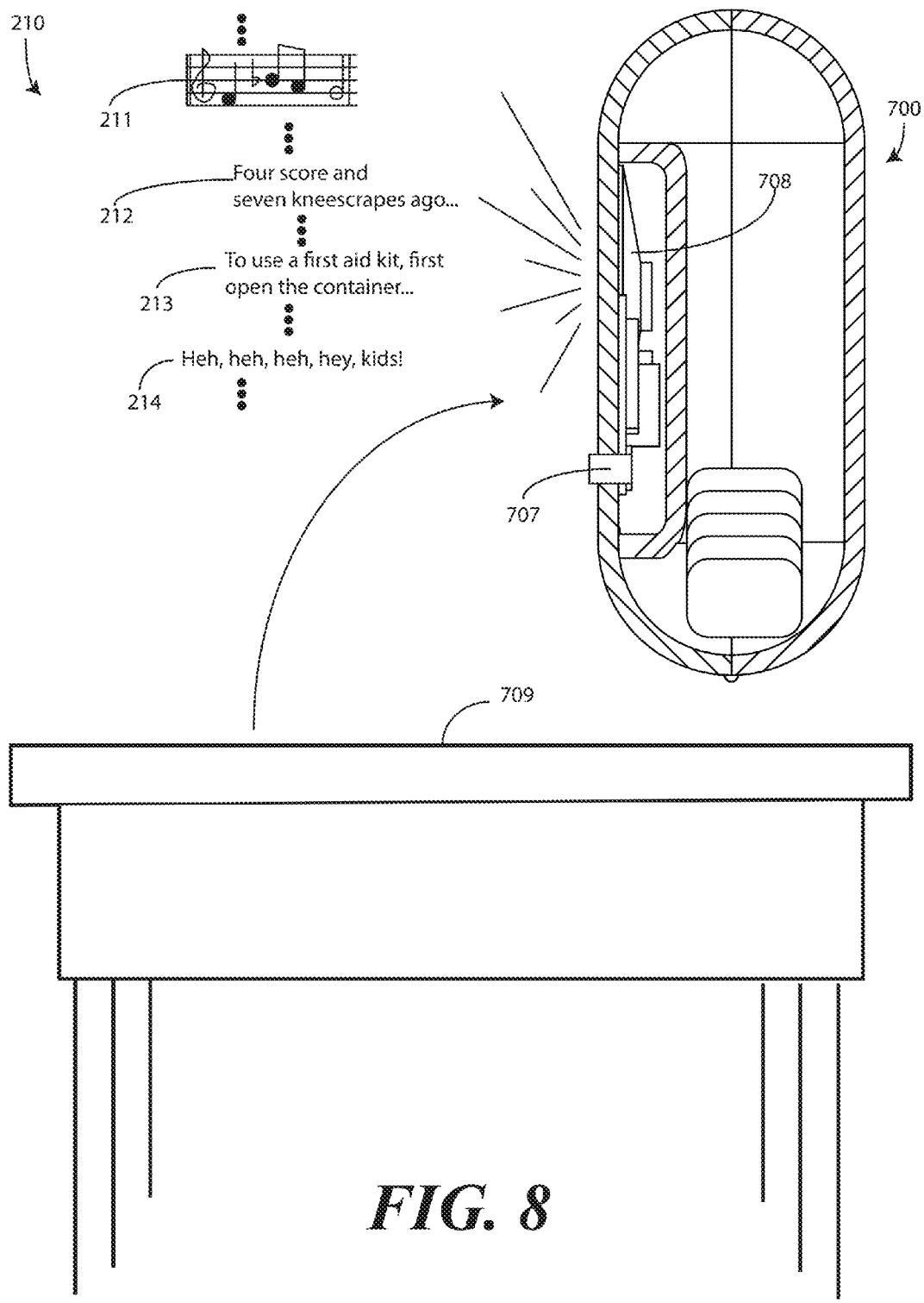

In the embodiment of FIG. 7, the container 700 includes a sensor 707 to detect the container 700 being disposed along a surface 706, which in this embodiment is a table 709. The container 700 also includes a sounder 708 that is operable with the sensor 707. In this embodiment, the sensor 707 is a pressure sensor that senses the force of gravity pulling the container 700 against the surface 706. As shown in FIG. 8, when the sensor 707 detects that the container 700 is removed from the surface 706, the sounder 708 can emit one or more pre-recorded sounds 210. As with previous embodiments, the pre-recorded sounds can be any of music 211, speech 212, instructional materials 213, amusing and fanciful utterances 214, or combinations thereof.

For example, in one embodiment when a user picks up the container 700, the pressure-sensing sensor 707 detects this and causes the sounder 708 to say, "Uh oh, did you hurt yourself? I sure am glad you are using a first aid kit. Open the lid to learn how to use the implements inside." Advantageously, this embodiment that causes the sounder 708 to emit sound when being picked up—and not opened—allows a curious youngster to play with a first aid kit and hear fun, interesting, and educational sounds without damaging or contaminating the first aid items held within the receiving cavity of the container. Also advantageously, this embodiment allows consumers to "demo" the container 700 in the store to determine whether the particular sounds emitted by the container 700 are suitable for their needs. For example, as noted above a manufacturer may offer several different containers, each emitting a different type of sound. One may be particularly well suited for boys, while another is particularly well suited for girls. By allowing the mother to test the sound emission without opening the container 700 in the store, she is able to confidently select the most appropriate container 700 for her child.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A container, comprising:
   a container body defining a receiving cavity to receive one or more first aid items, the container body comprising a first container body part pivotally coupled to a second container body part, the first container body part to pivot between a closed position enclosing the one or more first aid items and a radially displaced open position revealing the one or first aid items;

a sensor to detect the first container body part in or transitioning to the radially displaced open position, the sensor comprising:
  a spring contact switch; and
  an insulating first container body part;
  the insulating first container body part coupled to the first container body part;
  the insulating first container body part to translate when the first container body part pivots to the radially displaced open position;
  the spring contact switch to close when the insulating first container body part translates to actuate the sensor; and
a sounder, operable with the sensor, the sounder to emit one or more pre-recorded sounds when the sensor detects the first container body part in or transitioning to the radially displaced open position.

2. The container of claim 1, the sensor comprising a light detector, the first container body part to pivot from the closed position to the radially displaced open position to expose the light detector to light to actuate the light detector.

3. The container of claim 1, further comprising a partition dividing the receiving cavity into a first portion and a second portion, the one or more first aid items disposed within the first portion, the sounder disposed within the second portion.

4. The container of claim 1, further comprising a seal to retain the first container body part in the closed position until the seal is broken.

5. The container of claim 1, the one or more pre-recorded sounds one or more of music or speech.

6. The container of claim 1, the container comprising a first aid kit.

7. The container of claim 6, the one or more pre-recorded sounds comprising instructions for using one or more of the first aid kit or the one or more first aid items.

8. The container of claim 6, the sensor further to detect removal of at least one first aid item from the first aid kit, the one or more pre-recorded sounds comprising an aural identification of the at least one first aid item.

9. The container of claim 6, further comprising one or more lights, operable with the sensor, to illuminate when the sensor detects the first container body part in or transitioning to the radially displaced open position.

10. The container of claim 9, the one or more lights to flash when the sensor detects the first container body part in or transitioning to the radially displaced open position.

11. The container of claim 1, the sounder comprising:
  a memory device to store data corresponding to recorded sound expressions;
  a loudspeaker;
  one or more drivers, operable with the loudspeaker and the memory device, to deliver one or more of the recorded sound expressions to the loudspeaker; and
  an energy storage device.

12. A container, comprising:
  a container body defining a receiving cavity to receive one or more first aid items, the container body comprising a first container body part and a second container body part, the first container body part to transition between a closed position enclosing the one or more first aid items and an open position revealing the one or first aid items;
  a sensor to detect the container disposed along a surface, the sensor further to detect removal of at least one first aid item from the first aid kit; and
  a sounder, operable with the sensor, the sounder to emit one or more pre-recorded sounds when the sensor detects the container is removed from the surface, the one or more pre-recorded sounds comprising an aural identification of the at least one first aid item.

13. The container of claim 12, the one or more pre-recorded sounds one or more of music or speech.

14. The container of claim 12, the container comprising a first aid kit.

15. The container of claim 14, the one or more pre-recorded sounds comprising instructions for using one or more of the first aid kit or the one or more first aid items.

16. The container of claim 14, wherein when removal of the at least one first aid item from the first aid kit occurs, the one or more pre-recorded sounds further comprising an instruction for using the at least one first aid item.

17. The container of claim 14, further comprising one or more lights, operable with the sensor, to illuminate when the sensor detects the first container body part in or transitioning to the open position.

18. The container of claim 17, the one or more lights to flash when the sensor detects the first container body part in or transitioning to the open position.

19. The container of claim 12, the sounder comprising:
  a memory device to store data corresponding to recorded sound expressions;
  a loudspeaker;
  one or more drivers, operable with the loudspeaker and the memory device, to deliver one or more of the recorded sound expressions to the loudspeaker; and
  an energy storage device.

* * * * *